United States Patent [19]

Berenstein et al.

[11] Patent Number: 5,895,378
[45] Date of Patent: Apr. 20, 1999

[54] FLOW-DIRECTED CATHETER HAVING MULTIPLE TAPERS AND RADIO-OPAQUE MARKERS

[75] Inventors: Alejandro Berenstein, 1725 York Ave. #22F, New York, N.Y. 10128; Henry Nita, Milpitas, Calif.

[73] Assignees: Target Therapeutics, Inc., Fremont, Calif.; Alejandro Berenstein, New York, N.Y.

[21] Appl. No.: 08/865,372

[22] Filed: May 29, 1997

[51] Int. Cl.$^6$ .................................. A61M 25/00
[52] U.S. Cl. .................. 604/280; 604/264; 600/435; 138/100
[58] Field of Search .................. 604/280–282, 604/264, 51, 52, 53, 164, 170; 600/433, 435, 585; 138/100, 126, 142, 155; 606/194

[56] References Cited

U.S. PATENT DOCUMENTS

| | | |
|---|---|---|
| 3,094,124 | 6/1963 | Birtwell . |
| 4,022,191 | 5/1977 | Jamshidi . |
| 4,753,765 | 6/1988 | Pande . |
| 4,781,691 | 11/1988 | Gross . |
| 4,790,817 | 12/1988 | Luther . |
| 4,838,879 | 6/1989 | Tanabe et al. . |
| 5,069,673 | 12/1991 | Shwab . |
| 5,095,915 | 3/1992 | Engelson ........................ 128/772 |
| 5,141,487 | 8/1992 | Liprie ............................ 600/7 |
| 5,221,267 | 6/1993 | Folden ........................... 604/200 |
| 5,226,899 | 7/1993 | Lee et al. . |
| 5,267,574 | 12/1993 | Viera et al. ................... 128/772 |
| 5,336,205 | 8/1994 | Zenzen et al. ................. 604/280 |
| 5,364,374 | 11/1994 | Morrison et al. . |
| 5,417,665 | 5/1995 | De La Mata et al. . |
| 5,453,099 | 9/1995 | Lee et al. . |
| 5,478,326 | 12/1995 | Shiu . |
| 5,497,786 | 3/1996 | Urick ............................ 128/772 |
| 5,538,512 | 7/1996 | Zenzon et al. . |
| 5,542,937 | 8/1996 | Chee et al. ................... 604/280 |
| 5,569,222 | 10/1996 | Haselhorst et al. . |
| 5,601,538 | 2/1997 | Deem . |
| 5,614,136 | 3/1997 | Pepin et al. . |

FOREIGN PATENT DOCUMENTS

| | | |
|---|---|---|
| WO 96 38194 | 12/1996 | WIPO . |
| WO 97 48435 | 12/1997 | WIPO . |

*Primary Examiner*—Corrine M. McDermott
*Assistant Examiner*—Cris L. Rodriguez
*Attorney, Agent, or Firm*—Morrison & Foerster LLP

[57] ABSTRACT

This is a bloodflow-directable infusion catheter which may be used in cardiovascular and endovascular procedures to deliver diagnostic, therapeutic, or vaso-occlusive agents to a target site accessible through the vasculature. The device is a flow-directed infusion catheter having a variety of sections of different flexibilities with tapered junctions between those sections. Additionally, at least some of the inventive catheter's sections have radio-opaque markers at or near the distal end of the individual sections. The more distal section or sections of the inventive catheter may be severed from the catheter body by the physician user so that the remaining catheter has a suitable diameter for the chosen task and the resulting severed end has a radio-opaque marker showing the catheter's distalmost end.

9 Claims, 2 Drawing Sheets

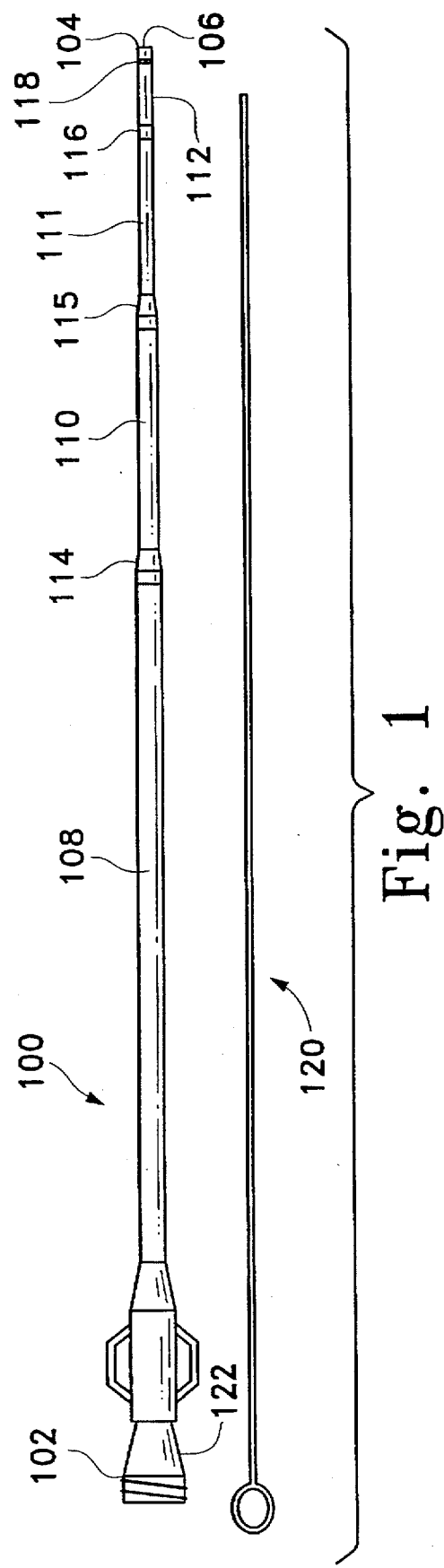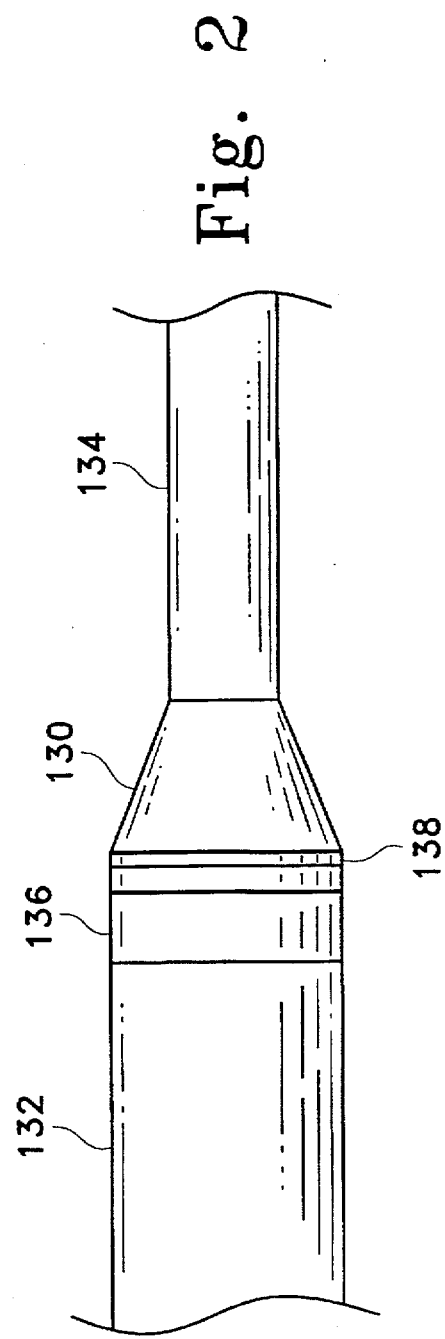

ns5,895,378

FLOW-DIRECTED CATHETER HAVING MULTIPLE TAPERS AND RADIO-OPAQUE MARKERS

FIELD OF THE INVENTION

This invention is a minimally invasive surgical device. In particular, the invention relates to an infusion catheter which may be used in cardiovascular and endovascular procedures to deliver diagnostic, therapeutic, or vaso-occlusive agents to a target site accessible through the vasculature. The device is a flow-directed infusion catheter having a variety of sections of different flexibilities with tapered junctions between those sections. Additionally, at least some of the inventive catheter's sections have radio-opaque markers at or near the distal end of the individual sections. The more distal section or sections of the inventive catheter may be severed from the catheter body by the physician user so that the remaining catheter has a suitable diameter for the chosen task and the resulting severed end has a radio-opaque marker showing the catheter's distal-most end.

BACKGROUND OF THE INVENTION

As the cost of classical surgery increases and the sophistication of minimally invasive surgical technology improves, the use of catheters as vehicles for delivering diagnostic and therapeutic agents to internal target sites has similarly increased. Of particular interest herein are catheters which may be used to access target sites through the circulatory system.

There are a number of generalized procedures for placing catheters within vessels in the body for accessing sites that are difficult to approach. Specifically, one such technique involves the use of a torqueable guidewire which, after insertion into the vasculature, is alternately rotated and advanced to the target site. As the guidewire is advanced, the catheter is then tracked along the wire until the distal end of the catheter is also positioned at the desired target site. An early example of this technique is described in U.S. Pat. No. 4,884,579, to Engelson. Although the technology involved in such a catheter is quite sophisticated, many consider an over-the-wire catheter to be a second choice when a highly time-sensitive situation is to be treated and when the vascular site to be accessed is in a path of high blood flow. This is due to the comparatively time-consuming nature of rotating and advancing the guidewire and then advancing the catheter over the guidewire through the vasculature.

An alternative is the use of a flow-directed catheter. One such flow-directed catheter technique includes employing a highly flexible catheter having an inflatable, but pre-punctured, balloon at its distal end. In use, the balloon is partially inflated, and carried by blood flow to the target site. During such a placement procedure, the balloon is continually inflated to replenish fluid leaking from the balloon. This technique, too, has major drawbacks, including the fact that the catheter material is so flexible that the catheter cannot be pushed from the proximal end without buckling some portion of the catheter. Instead, the catheter must be advanced using injected fluid to inflate the balloon in order to propel the catheter to the target site. There is always the risk of rupture of a vessel by a balloon that has been too highly inflated.

Other flow-directed catheters have also been proposed which do not use such leaking balloon technology. Specifically, the catheters are so flexible at their distal and mid regions that they are able to be carried by blood flowing to a target site. Examples of such products are described in U.S. Pat. No. 5,336,205 (to Zenzen et al.) and U.S. Pat. No. 5,538,512 (to Zenzen et al.). These catheters have in common the presence of a relatively stiff tapered proximal segment, a relatively flexible and strong distal segment, and a transition section between those proximal and distal segments which is intermediate in flexibility. The distal segment has a burst pressure release of 195 psi and is made of a material that shows exceptional deflection when a minor force is placed upon such distal portion.

Neither of these patented devices have the structure of the device described below.

SUMMARY OF THE INVENTION

This invention is a flow-directed infusion catheter for placement within the vasculature. In particular, it may be delivered to a target site by means of blood flow to that site. It may be used to deliver diagnostics, therapeutics, or vaso-occlusive agents via tortuous, small vessel pathways to the selected site. The infusion catheter has an elongate tubular body having proximal and distal ends and a lumen extending between those ends.

The elongate tubular body is formed of a comparatively stiff proximal segment, a comparatively flexible and fairly strong distal segment, and at least one transition section between the proximal and distal segments having flexibilities which are desirably intermediate in value between the flexibility between the flexibility of the distal and proximal segments. It may have more segments if such is desired. Also desirably, the various segments have decreasingly smaller diameters as the distal end of the catheter is approached. The more distal end of each of the segments preferably includes a radio-opaque marker.

The devices typically have a tapered joint between each of the noted segments. Highly preferred is a structure which has been annealed so that the thermoplastics found at the various joints have been smoothed and the crystallinity of the constituent polymers found in the various catheter segments has been lessened.

The materials preferably making up the various catheter segments are desirably thermoplastics, particularly polyvinylchloride (PVC) or polyurethane. Also desirably, the polymers may contain a radio-opacifier such as bismuth subcarbonate. Each of the segments may contain a radio-opaque additive but is especially preferred that it be placed in the distal and middle segments.

The catheter is configured so that a user physician may cut one or more distally located sections from the catheter assembly just prior to use so to select a specific distal diameter; yet the resulting catheter assembly still retains a radio-opaque marker at that severed end.

It is highly desirable that the catheter assembly be of such flexibility that it be combined with a stylet for delivery in a guiding catheter to a region of the body through a larger guiding catheter. Once the distal end of the inventive catheter is near the distal end of the guide catheter, the stylet is removed and only then is the blood flow used to extend the inventive catheter to its target site.

Finally, this catheter assembly may be used with a guidewire in place of the stylet or to augment it. The optional guidewire may be used as a stiffener in the manner of a stylet or the guidewire may be used to guide the tip of the catheter assembly into regions which are not "high-flow" regions. The guidewire may be used to re-direct the catheter assembly distal tip into a selected site.

The interior and exterior of the device may be coated with a hydrophilic coating.

BRIEF DESCRIPTION OF THE DRAWINGS

FIG. 1 shows, in side-view, a flow-directed catheter made according to the preferred embodiment of the invention.

FIG. 2 shows a close-up, side-view of a junction suitable for this inventive catheter.

DESCRIPTION OF THE INVENTION

Figure 3A:
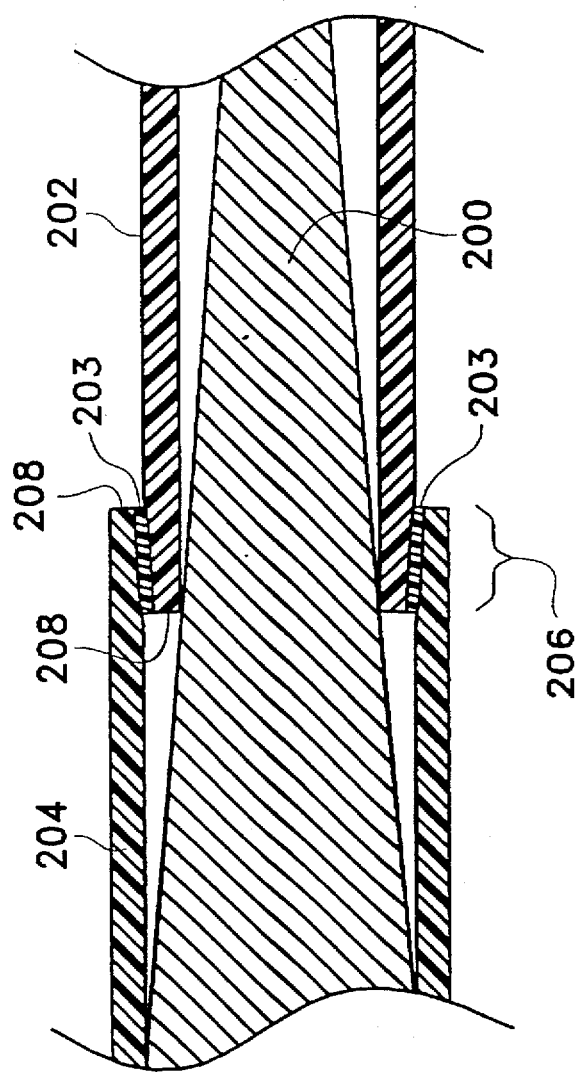
FIG. 3A shows, in cross-section, a junction of the inventive catheter during its assembly using a tapered mandrel.

FIG. 1 shows a flow-directed infusion catheter (100) made according to a preferred embodiment of the invention. The catheter (100) has an elongate tubular body with a proximal end (102) and a distal end (104) and an inner lumen (106) extending between those ends. For this variation of the inventive catheter (100), the tubular body has four segments; a comparatively stiff proximal segment (108), a comparatively more first flexible intermediate section (110), a comparatively more second flexible intermediate section (111), and a most flexible distal segment (112). Between the proximal segment (108) and the first mid segment (110) lies a tapering joint (114). Similarly, between the first mid segment (110) and second mid segment (111) lies a tapering joint (115).

Between the second mid segment (111) and distal segment (112) lies a tapering joint (116). The flexible distal segment (112) may have one or more radio-opaque bands (118) allowing clear visualization of the catheter distal tip using fluoroscopy.

The flexible distal segment (112) has an open end (104) which allows for the infusion of diagnostic, therapeutic, or vaso-occlusive agents into the target site. The flexible distal segment (112) may be made of a polymer which is inherently quite springy and flexible and biologically compatible such as polyvinylchloride (PVC), polyurethane, silicones, or various block copolymers of polyamides with these polymers or blends or alloys of them. This segment may be doped with radio-opaque materials such as barium sulfate, bismuth trioxide, bismuth subcarbonate, powdered tungsten, powdered tantalum, or the like. Preferred is bismuth subcarbonate. It is typical that contents of this section may include between 10% and 30% by weight of the radio-opaque material, preferably 20–25%. The preferred polymers are polyurethane and PVC. Most preferred is PVC. The range of hardness for the materials of this section are Shore 55A to 75A, preferably 60A to 70A, and most preferably in the neighborhood of Shore 65A.

The distal segment (112) typically makes up between 5% and 25% of the total length of the tubular member and is generally between 5 and 40 cm. in length. Most preferably, it is between 10–30 cm. in length. The outer diameter of distal segment (112) is preferably between 0.75 F and 2.5 F. Most preferably is an outer diameter in the neighborhood of 0.75 F and 2 F, most preferred is 1.5 F. It should be noted that this is an extremely small catheter diameter.

First and second mid segments (110, 111) may be made of the same general materials as is the distal segment. Of course, the flexibility of the material making up these middle segments is preferably moderately more stiff than is the distal section. This is to say that the flexural modulus of the polymer making up the section is between Shore 65A and 85A, preferably 67A and 77A, and most preferably about 72A. The length of each midsection (110, 111) is each typically between 10–20% of the overall length of the tubular member. The physical length of each is typically between 15–40 cm. and preferably between 15–30 cm. The outer diameter of each mid section (110) desirably is between 1.5 F and 3 F, preferably between 1.5 F and 2.6 F.

Proximal segment (108) similarly may be made of a polymeric material such as those discussed above with regard to the other two segments. However, since it is relatively more stiff than the other two sections, it may also be produced of a material such as a polyamides (Nylon) and polyethylene, e.g. high density, or polypropylene. Preferably, on the basis of compatibility with the preferred polymers in the other segments, the proximal segment is PVC or polyurethane, preferably PVC. The proximal segment (108) may also comprise a braided shaft (a polymer outer core with a metallic mesh inner core) or a coil (a helically wound wire or ribbon on a polymer core further covered by a polymer outer cover). The proximal segment typically makes up between 60–80% of the total length of the tubular member and is typically between 100–140 cm. in length, preferably 105–120 cm. in length. The outer diameter is larger than that of the first middle section (110) and typically is between 2.9 F and 3.5 F, preferably 2.7 F to 3.2 F, and most preferably 3 F. The wall thickness is preferably between about 4 mils and 12 mils.

The polymers used in proximal section (108) typically are blended to include some amount of one or more of the radio-opaque powdered materials discussed above.

Highly preferred in this variation of the invention is the use of a distal section (112), first midsection (110), second midsection (111), and proximal section (108) which are of a substantially constant diameter and in which the joints (114), (115), and (116) are tapered. Use of tapered joints provide for ease of assembly and allow for a smooth transition between the segments.

A long stylet (120) is also shown. The stylet (120) approximates, but is typically slightly longer than, the overall length of the catheter assembly (100) but unlike a guidewire is not used to precede the catheter through the vasculature. This is so because of the absence of a taper or shapeable tip on the stylet and the absence of a soft distal end. Stylet (120) is placed interior to the catheter assembly (100) during the time it is initially into the body. That is to say that the stylet provides sufficient stiffness to allow to be manipulated through a guiding catheter assembly.

The catheter assembly may be used with a guidewire in place of the stylet or to augment that guidewire. The optional guidewire may be used as a stiffener in the manner of a stylet or the guidewire may be used to guide the tip of the catheter assembly into regions which are not "high-flow" regions. The guidewire may be used to re-direct the catheter assembly distal tip into a selected site.

The most proximal portion of the catheter includes the typical means (122) for joining the proximal end of the catheter to other devices using, e.g., helically cut threads or the like.

Central to this invention is the use of a radio-opaque marker proximally of each tapered junction. Although the variation of the inventive catheter shown in FIG. 1 has four sections, we intend the invention to include catheters of two or more sections, preferably three or more sections.

FIG. 2 shows a close-up of a junction (130) between a larger diameter section (132) and a smaller diameter section (134). The radio-opaque member (136) located distally in the larger diameter section (132) is also shown. Noted above is the indication that the inventive catheter may be cut at the junction to allow the user physician to cut the catheter at the junction and choose a catheter diameter and length suitable for a particular situation. FIG. 2 shows an optional visual marker (138) to allow that user to cut the catheter cleanly without endangering the adjacent radio-opaque marker. The optional marker may be introduced in a variety of ways, e.g., by molding an independent and discrete band at the appropriate point in the joint or by using a colored adhesive at the contact point between the two polymeric layers otherwise making up the joint.

Although the disclosure herein specifies with some particularity a highly preferred way of producing a "junction" between adjacent catheter sections, we do not intend to be so limited. The term "junction" is meant to include other ways of making the junction and the structure so-produced. For instance, the junction may be extruded, may include a short section or point along a tapered tubular member forming an otherwise bloodflow-directable catheter. Specifically, the junction need form a joint between tubular members of different diameters.

FIG. 3A shows a first step in producing the tapered joints between the various catheter sections. FIG. 3A shows a tapered mandrel (200) which typically would be made of a metal such as stainless steel or other heat-resistant material. A smaller diameter polymeric tubing (202), an optional contrasting color marker insert (203), and a larger diameter polymeric tubing (204) are shown placed there. The overlap (206) between larger polymeric tubing (204) and smaller polymeric tubing (202) is shown therein. Overlap (206) may be of any convenient length but we have found that for a catheter of this type, an overlap of 0.05–3 mm. is desirable. For PVC, an overlap of about 1 mm. is highly desirable. The ends (208) of the respective polymeric tubing (202) and (204) may be chamfered or rounded if so desired.

The tapered mandrel is for the specific purpose of providing shape to the overlap (206) during the step of heating that overlap (206).

Figure 3B:
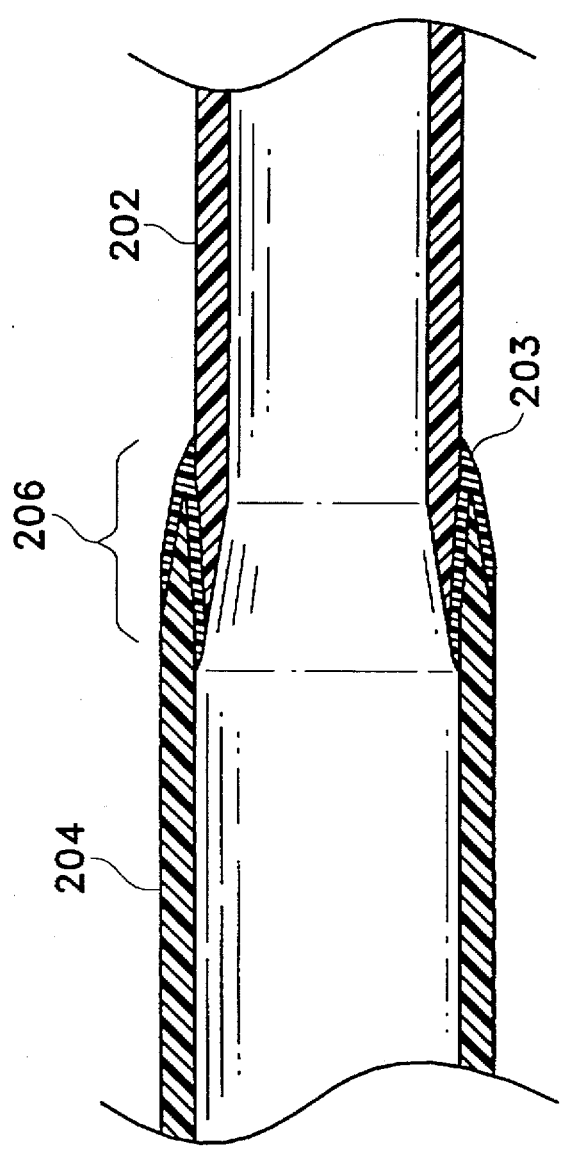
FIG. 3B shows the catheter joint of FIG. 3A after the assembly step is completed.

FIG. 3B shows the overall shape of the fused overlap joint (206) after heating. The inner profile of overlap (206) generally follows that of tapered mandrel (200). The visual marker (203) is shown in the cut-away between the corresponding layers of the polymer from the large diameter tubing (204) and the small diameter tubing (202). For optimum operation as a marker, the contrasting color polymer should show consistent amount around the periphery of the proximal end of the junction. The construction of overlap (206) during the heating step must be done with some care. We have found, for instance, that when fusing a joint between two sections of Shore 72A PVC having 23% bismuth carbonate with a section of tubing having a Shore hardness of 65A also containing 23% bismuth carbonate, an acceptable joint is readily formed at a temperature of 375° F. for 10–15 seconds. For harder materials, e.g., a 1 mm. overlap joint of Shore 77D PVC with 16% bismuth carbonate and a smaller tubing of Shore 72A PVC with 23% bismuth carbonate, a heating step of 415° F. for 10–15 seconds is adequate.

We have also found that when using either PVC or a polyurethane, particularly when the PVC's are infused with plasticizers such as epoxidized soybean oil, the catheter assembly is provided with substantial added flexibility and conformability where the catheter is "annealed" after the tapered joints have been produced.

The exterior and interior surfaces of catheter assembly may be treated with a hydrophilic covering much as recited in the patent to Zenzen et al. (U.S. Pat. No. 5,538,512), the entirety of which is incorporated by reference.

Although preferred embodiments of the invention have been described herein, it will be recognized that a variety of equivalent changes and modifications may be made to the invention and yet still be within the concept of the claims recited below.

We claim as our invention:

1. A single lumen, bloodflow-directable catheter which may be severed at a number of selected points to provide a thus-severed catheter with a radio-opaque marker near said severed points, which catheter may be directed to a target site within the vasculature of the human body by bloodflow within that vasculature, said catheter having a catheter distal end and a catheter proximal end and comprising:

a.) a plurality of polymeric tubular segments each having a proximal end, a distal end, a diameter, and a radio-opaque member adjacent each said distal end and b.) a plurality of junctions each joining a pair of said plurality of polymeric tubular segments such that each junction joins one of said polymeric tubular segments proximal end to one of said polymeric tubular segments distal end and wherein said plurality of polymeric tubular segments and junctions form said single lumen.

2. The single lumen bloodflow-directable catheter of claim 1 wherein each of said plurality of polymeric tubular segments have a different diameter.

3. The single lumen bloodflow-directable catheter of claim 2 wherein said plurality of polymeric tubular segments having different diameters are arranged so that those diameters decrease distally.

4. The single lumen bloodflow-directable catheter of claim 3 wherein each of said plurality of junctions is tapered.

5. The single lumen bloodflow-directable catheter of claim 4 wherein said tapered joints are molded of overlapping portions respectively of said tubular segment proximal end and said tubular segment distal end.

6. The single lumen bloodflow-directable catheter of claim 5 further comprising a visual marker adjacent to and proximal of each said joint for marking a severance point.

7. The single lumen bloodflow-directable catheter of claim 1 wherein each of said plurality of junctions is tapered.

8. The single lumen bloodflow-directable catheter of claim 1 further comprising a stylet at least partially located within said lumen.

9. The single lumen bloodflow-directable catheter of claim 1 further comprising a guidewire at least partially located within said lumen.

* * * * *